United States Patent [19]

Rivier et al.

[11] Patent Number: 4,703,035
[45] Date of Patent: * Oct. 27, 1987

[54] HUMAN PANCREATIC GRF AMIDATED FRAGMENTS

[75] Inventors: Jean E. F. Rivier, La Jolla; Joachim Spiess, Encinitas; Wylie W. Vale, Jr., La Jolla, all of Calif.

[73] Assignee: The Salk Institute for Biological Studies, San Diego, Calif.

[ * ] Notice: The portion of the term of this patent subsequent to May 14, 2002 has been disclaimed.

[21] Appl. No.: 782,912

[22] Filed: Oct. 2, 1985

Related U.S. Application Data

[63] Continuation-in-part of Ser. No. 432,663, Oct. 4, 1982, Pat. No. 4,563,352.

[51] Int. Cl.⁴ .................... A61K 37/36; A61K 37/43; C07K 7/10
[52] U.S. Cl. ........................................ 514/12; 530/324
[58] Field of Search ........................... 514/12; 530/324

[56] References Cited

U.S. PATENT DOCUMENTS 4,517,181  5/1985  Ling et al. ............................. 514/12
4,563,352  1/1986  Rivier et al. .......................... 514/12

Primary Examiner—Delbert R. Phillips
Attorney, Agent, or Firm—Fitch, Even, Tabin & Flannery

[57] ABSTRACT

Surprisingly active fragments of human pancreatic GRF have been synthesized which exhibit good biological activity. These synthetic peptides are extremely potent in stimulating the release of pituitary GH in humans and in nonhuman animals and have the general formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Y wherein Y is $NH_2$, Gln-$NH_2$, Gln-Gln-$NH_2$ or Gln-Gln-Gly-$NH_2$. Two such fragments have been tested, namely the 29 and the 32 N-terminal residue sequences that are amidated at the C-terminus. These peptides, as well as nontoxic salts thereof, may be administered therapeutically to animals, including humans.

8 Claims, No Drawings

HUMAN PANCREATIC GRF AMIDATED FRAGMENTS

This invention was made with Government support under Grant No. AM-26741 awarded by the National Institutes of Health. The Government has certain rights in this invention.

This application is a continuation-in-part of our earlier-filed patent application U.S. Ser. No. 432,663, filed Oct. 4, 1982, now U.S. Pat. No. 4,563,352.

The present invention relates to a peptide having influence on the function of the pituitary gland in humans and other animals, particularly mammals. In particular, the present invention is directed to peptides which promote the release of growth hormone by the pituitary gland.

BACKGROUND OF THE INVENTION

Physiologists have long recognized that the hypothalamus controls all the secretory functions of the adenohypophysis with the hypothalamus producing special polypeptides which trigger the secretion of each pituitary hormone. An inhibitory factor was earlier characterized in the form of somatostatin which inhibits the secretion of growth hormone(GH).

A corresponding hypothalamic releasing factor for pituitary GH was long sought after, and in 1982, a polypeptide was isolated from an extract from a human pancreatic tumor, purified, characterized, synthesized and tested which promotes the release of GH by the pituitary. The formula of this 40-residue peptide is as follows: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-OH. The peptide is hereinafter referred to as hpGRF (for human pancreatic tumor GH releasing factor). A 44-residue amidated version of this peptide was isolated from another tumor which included Arg-Ala-Arg-Leu-NH$_2$ at the C-terminus.

SUMMARY OF THE INVENTION

Surprisingly, it has now been found that there are fragments of hpGRF, such as those which include either the 29 N-terminal residues or the 32 N-terminal residues, which have their C-terminus amidated and which show biological potency equal to or greater than that of the native 40-residue peptide. Thus, the invention provides synthetic hpGRF fragments of 32 residues or less which are amidated at the C-terminus and which include the N-terminal peptide sequence through at least the first 29 residues.

Pharmaceutical compositions in accordance with the invention include such biologically active amidated fragments of hpGRF, or a nontoxic salt of the foregoing, dispersed in a pharmaceutically acceptable liquid or solid carrier. Such compositions can be used in clinical medicine, both human and veterinary, for administration for therapeutic purposes, and also diagnostically.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. Where the amino acid residue has isomeric forms, it is the L-form of the amino acid that is represented unless otherwise expressly indicated.

The invention provides synthetic hpGRF peptides having the following formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Y wherein Y is NH$_2$, Gln-NH$_2$, Gln-Gln-NH$_2$ or Gln-Gln-Gly-NH$_2$, or a nontoxic salt thereof.

The peptides are synthesized by a suitable method, such as by exclusively solid-phase techniques, by partial solid-phase techniques, by fragment condensation, by classical solution couplings, or by the employment of recently developed recombinant DNA techniques for the fragments containing only L-isomer residues. For example, the techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603 issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Synthesis by the use of recombinant DNA techniques, for purposes of this application,, should be understood to include the suitable employment of a structural gene coding the desired form of hpGRF fragment. The synthetic hpGRF fragment may be obtained by transforming a microorganism using an expression vector including a promoter and operator together with such structural gene and causing such transformed microorganism to express the hpGRF fragment. A non-human animal may also be used to produce the hpGRF fragment by gene-farming using such a structural gene and the general techniques set forth in U.S. Pat. No. 4,276,282 issued June 30, 1981 or using microinjection of embryos as described in WO82/01783 published May 26, 1983 and WO82/04443 published Dec. 23, 1982. The synthetic hpGRF fragment may also be produced directly in the animal for which accelerated growth is intended by the techniques described in the two WO publications, in which case the gene sequence used would be such as to amidate the C-terminus. In other instances, it is also feasible to recover the peptide in its free acid form and either chemically or enzymatically effect amidation.

Common to chemical or coupling syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula: $X^1$-Tyr($X^2$)-Ala-Asp($X^3$)-Ala-Ile-Phe-Thr($X^4$)-Asn($X^5$)-Ser($X^4$)-Tyr($X^2$)-Arg($X^6$)-Lys($X^7$)-Val-Leu-Gly-Gln($x^5$)-Leu-Ser($X^4$)-Ala-Arg($X^6$)-Lys($X^7$)-Leu-Leu-Gln($X^5$)-

Asp($X^3$)-Ile-Met-Ser($X^4$)-Arg($X^6$)-Gln($X^5$)-Gln($X^5$)-Gly-$X^8$ (or sequences appropriately shortened at the C-terminus) wherein: $X^1$ is either hydrogen or an a-amino protecting group. The a-amino protecting groups contemplated by $X^1$ are those known to be useful in the art of step-wise synthesis of polypeptides. Among the classes of a-amino protecting groups covered by $X^1$ are (1) acyl-type protecting groups, such as formyl, trifluoroacetyl, phthalyl, toluenesulfonyl(Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethyloxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl; (7) trialkylsilane groups, such as trimethylsilane. The preferred a-amino protecting group is BOC.

$X^2$ is a protecting group for the phenolic hydroxyl group of Tyr selected from the group consisting of tetrahydropyranyl, tert-butyl, trityl, Bzl, CBZ, 4Br-CBZ and 2, 6-dichlorobenzyl(DCB). The preferred protecting group is 2, 6-dichlorobenzyl. $X^2$ can be hydrogen which means that there is no protecting group on the hydroxyl group.

$X^3$ is hydrogen or an ester-forming protecting group for the carboxyl group of Asp and is selected from the group consisting of benzyl(OBzl), 2, 6-dichlorobenzyl, methyl and ethyl.

$X^4$ is a protecting group for the hydroxyl group of Thr or Ser and is selected from the group consisting of acetyl, benzoyl, tert-butyl, trityl, tetrahydropyranyl, Bzl, 2, 6-dichlorobenzyl and CBZ. The preferred protecting group is Bzl. $X^4$ can be hydrogen, which means there is no protecting group on the hydroxyl group.

$X^5$ is hydrogen or a protecting group for the side chain amido group of Asn or Gln, and it is preferably xanthyl(Xan).

$X^6$ is a protecting group for the guanidino group of Arg selected from the group consisting of nitro, Tos, CBZ, adamantyloxycarbonyl, and BOC, or is hydrogen;

$X^7$ is hydrogen or a protecting group for the side chain amino substituent of Lys. Illustrative of suitable side chain amino protecting groups are 2-chlorobenzyloxycarbonyl (2Cl-Z), Tos, t-amyloxycarbonyl and BOC.

Met can optionally be protected by oxygen, but is preferably left unprotected.

The selection of a side chain amino protecting group is not critical except that it must be one which is not removed during deprotection of the a-amino groups during the synthesis. Hence, the a-amino protecting group and the side chain amino protecting group should not be the same.

$X^8$ can be a suitable protecting group for the C-terminal carboxyl group, such as the ester-forming group that can be removed without the removal of the group $X^3$ on the Asp residue, or an anchoring bond used in solid-phase synthesis for linking to a solid resin support, or is $NH_2$. When a solid resin support is used, it should have the formulae: -NH-benzhydrylamine (BHA) resin support or -NH-paramethylbenzhydrylamine (MBHA) resin support. Use of BHA or MBHA resin is preferred because cleavage directly gives the unsubstituted amide. In case the N-methyl amide is desired, it can be generated from an N-methyl BHA resin.

In the formula for the intermediate, at least one of the X-groups is a protecting group or $X^8$ includes resin support.

In selecting a particular side chain protecting group to be used in the synthesis of the peptides, the following rules are followed: (a) the protecting group must retain its protecting properties and not be split off under coupling conditions, (b) the protecting group should be stable to the reagent and, with the exception of Xan, should be stable under the reaction conditions selected for removing the a-amino protecting group at each step of the synthesis, and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1963), although other equivalent chemical syntheses known in the art can also be used as previously mentioned. Solid-phase synthesis is commenced from the C-terminal end of the peptide by coupling a protected a-amino acid to a suitable resin. Such a starting material for the 32-residue peptide can be prepared by attaching a-amino-protected Gly by an amide bond to a BHA resin or MBHA resin; BHA and MBHA resin supports are commercially available.

Gly, protected by BOC, can be coupled to the chloromethylated resin according to the procedure of Horiki, K. et. al. *Chemistry Letters* 1978, 165–168, published by the Chemical Society of Japan. Following the coupling of BOC-Gly to the resin support, the a-amino protecting group is removed, as by using trifluoroacetic acid(TFA) in methylene chloride, TFA alone or HCl in dioxane. The deprotection is carried out at a temperature between about 0° C. and room temperature. Other standard cleaving reagents and conditions for removal of specific a-amino protecting groups may be used as described in Schroder & Lubke, "The Peptides", 1 pp 72–75 (Academic Press 1965).

After removal of the a-amino protecting group of Gly, the remaining a-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N, N'-dicyclohexyl carbodiimide(DCCI).

The activating reagents used in the solid phase synthesis of the peptides are well known in the peptide art. Examples of suitable activating reagents are carbodiimides, such as N, N'-diisopropyl carbodiimide, N-ethyl-N'-(3-dimethylaminopropyl)carbodiimide. Other activating reagents and their use in peptide coupling are described by Barany & Merrifield, in Chapter I, *The Peptides*, pp. 122–129 (1979) and by Kapoor, *J. Phar. Sci.*, 59, pp 1–27 (1970).

Each protected amino acid or amino acid sequence is introduced into the solid phase reactor in about a threefold or greater excess, and the coupling may be carried out in a medium of dimethylformamide(DMF):CH$_2$Cl$_2$ (1:1) or in DMF or CH$_2$Cl$_2$ alone. In cases where incomplete coupling occurs, the coupling procedure is repeated before removal of the a-amino protecting group prior to the coupling of the next amino acid. The success of the coupling reaction at each stage of the synthesis is monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927–1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$ and $X^7$, the anchoring bond $X^8$ and the a-amino protecting group $X^1$, to obtain the peptide in the form of the free acid. Because Met is present in the sequence, the BOC protecting group is preferably first cleaved using trifluoroacetic acid (TFA)/ethanedithiol prior to cleaving the peptide from the resin with HF to eliminate potential S-alkylation. When using HF for cleaving, anisole and either methylethyl sulfide or dimethyl sulfide are included in the reaction vessel for scavenging.

The following Example sets forth the preferred method for synthesizing hpGRF amidated fragments by the solid-phase technique. It will of course be appreciated that the synthesis of a correspondingly shorter peptide fragment is effected in the same manner by merely eliminating the requisite number of amino acids at the C-terminus.

EXAMPLE I

The synthesis of hpGRF(1–32)-NH$_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-NH$_2$ is conducted in a stepwise synthesizer on a MBHA hydrochloride resin, such as that available from Bachem, Inc., having a substitution range of about 0.1 to 0.5 mmoles/g. resin. Coupling of BOC-Gly to the resin is performed by the general procedure set forth below in Schedules A and B which is used throughout the synthesis, and it results in the substitution of about 0.35 mmol. Gly per gram of resin. All solvents that are used are carefully degassed by sparging with an inert gas, e.g. helium or nitrogen, to insure the absence of oxygen that might undesirably oxidize the sulfur of the Met residue.

After deblocking and neutralization, the peptide chain is built step-by-step on the resin. Deblocking, neutralization and addition of each amino acid is performed in general accordance with the procedure set forth in detail in Vale et al. U.S. Pat. No. 4, 292, 313.

Deblocking is preferably carried out in accordance with Schedule A which follows:

| SCHEDULE A | |
|---|---|
| Reagent | Mixing time (Min.) |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |

| -continued SCHEDULE A | |
|---|---|
| Reagent | Mixing time (Min.) |
| 7. MeOH (twice) | 0.5 |
| 8. CH$_2$Cl$_2$ (twice) | 0.5 |

The couplings are preferably carried out as set out in schedule B which follows:

| SCHEDULE B | |
|---|---|
| Reagent | Mixing time (Min.) |
| 9. DCCI | — |
| 10. Boc-amino acid | 50–90 |
| 11. MeOH (twice) | 0.5 |
| 12. CH$_2$Cl$_2$ (twice) | 0.5 |
| 13. Ac$_2$O (3M) in CH$_2$Cl$_2$ | 15.0 |
| 14. CH$_2$Cl$_2$ | 0.5 |
| 15. MeOH | 0.5 |
| 16. CH$_2$Cl$_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(TOS) is being coupled, a mixture of 50% DMF and methylene chloride is used. Bzl ether is used as the hydroxyl side-chain protecting group for Ser and Thr. P-nitrophenyl ester (ONp) is used to activate the carboxyl end of Asn or Gln, and for example, BOC-Asn(ONp) is coupled overnight using one equivalent of HOBt in a 50% mixture of DMF and methylene chloride, in which case no DCC is added. The amido group of Asn or Gln is protected by Xan when DCC coupling is used instead of the active ester method. 2Cl-Z is used as the protecting group for the Lys side chain. Tos is used to protect the guanidino group of Arg, and the Asp carboxyl group is protected as OBzl. The phenolic hydroxyl group of Tyr is protected with DCB. At the end of the synthesis, the following composition is obtained: $X^1$-Tyr($X^2$)-Ala-Asp($X^3$)-Ala-Ile-Phe-Thr($X^4$)-Asn($X^5$)-Ser($X^4$)-Tyr($X^2$)-Arg($X^6$)-Lys($X^7$)-Val-Leu-Gly-Gln($x^5$)Leu-Ser($X^4$)-Ala-Arg($X^6$)-Lys($X^7$)-Leu-Leu-Gln ($X^5$) wherein $X^1$ is BOC, $X^2$ is DCB, $X^3$ is benzyl ester, $X^4$ is Bzl, $X^5$ is Xan, $X^6$ is Tos, $X^7$ is 2Cl-Z and $X^8$ is -NH-resin support. Xan may have been partially or totally removed by TFA treatment used to deblock the a-amino protecting group.

After the final Tyr residue has been coupled to the resin, BOC is removed with 60% TFA in CH$_2$Cl$_2$In order to cleave and deprotect the remaining protected peptide-resin, it is treated with 1.5 ml. anisole, 0.5 ml. methylethylsulfide and 15 ml. HF per gram of peptide-resin, at $-20°$ C. for about one-half hour and at $0°$ C. for about one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The cleaved and deprotected peptide is then dissolved in 0–5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp 125–8 and Marki et al. *J. Am. Chem. Soc.* 103, 317 (1981). In summary cartridges fitting Waters Associates prep LC-500 are packed with 15–20 μg, C$_{18}$ Silica from Vydac (300A.). A gradient of $CH_3CN$ in TEAP is generated by a low pressure Eldex gradient maker, as described in Rivier, J., *J. Liq. Chromatography* 1, 343-367 (1978). The chromatographic fractions are carefully monitored by HPLC, and only the fractions showing substantial purity are pooled. Desalting of the purified fractions independently checked for purity, is achieved using a gradient of $CH_3CN$ in 0.1% TFA. The center cut is then lyophilized to yield the desired peptide, the purity of which can be greater than 98%.

EXAMPLE II

The synthesis of the hpGRF fragment, hpGRF(1-31)-$NH_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-$NH_2$ is conducted in a stepwise manner using a Beckman 990 Peptide Synthesizer on an MBHA resin in the manner described in Example I. This analog is judged to be substantially pure using TLC and HPLC.

EXAMPLE III

The synthesis of the hpGRF fragment hpGRF(1-29)-$NH_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-$NH_2$ is conducted in a stepwise manner using a Beckman 990 Peptide Synthesizer on an MBHA resin in the manner described in Example I. The peptide is judged to be substantially pure using TLC and HPLC.

EXAMPLE IV

The synthesis of the hpGRF fragment hpGRF(1-30) having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-$NH_2$ is conducted in a stepwise manner using a Beckman 990 Peptide Synthesizer on an MBHA resin in the manner described in Example I. The peptide is judged to be substantially pure using TLC and HPLC.

The two synthetic peptides prepared in Examples I and III are compared with purified native hpGRF in in vitro assays and are found to exhibit similar potencies for the secretion of GH and similar intrinsic activities.

To determine the effectiveness of the various synthetic peptides to promote the release of growth hormone, in vitro assays are carried out using synthetic hpGRF(1-40)-OH as a standard (because it is the equivalent of the native peptide) in side-by-side comparison with equimolar concentrations of the various other analogs and fragments synthesized. Cultures are used which include cells of rat pituitary glands removed some four to five days previously. Cultures which are considered optimal for the secretion of growth hormone are used for the comparative testing, in the general manner described in Vale et al. *Endocrinology*, 91, 562-572 (1972). Incubation with the substance to be tested is carried out for 3 to 4 hours, and aliquots of the culture medium are removed and processed to measure their contents in immunoreactive GH(ir GH) by a well-characterized radioimmunoassay.

The results of this comparative testing for equimolar concentrations are shown in Table I.

TABLE I

| Peptide | Comparison % |
|---|---|
| hpGRF(1-40)-OH (standard for this test) | 100% |
| hpGRF(1-32)-$NH_2$ | 140% |
| hpGRF(1-29)-$NH_2$ | 106% |

In vitro testing of these synthetic peptides shows that the $EC_{50}$ varies from 20-100 picomolar and the lowest effective concentration to be 3-8 picomolar. The maximum effective concentration for hpGRF(1-40)-OH was about 1 nanomolar.

In addition to the in vitro tests for secretion of growth hormone, in vivo experiments are also run by injecting the synthetic peptide through an indwelling catheter into freely running normal male rats. Animals are pretreated with FLA-63, a dopamine hydroxylase inhibitor that suppresses spontaneous GH secretion without affecting the response to exogenous GRF. Blood samples are taken through the same catheter immediately prior to and 5 and 20 minutes after injections; GH levels in blood are measured by radioimmunoassay. The results show that synthetic hpGRF(1-40)-OH and other analogs are powerful stimulators of the secretion of pituitary GH. Dosages between about 40 nanograms and about 25 micrograms per Kg. of body weight were found to be effective.

Further testing shows that the synthetic hpGRF fragments synthesized in Examples I and III exhibit full intrinsic biological activity of hpGRF(1-40)-OH.

Synthetic hpGRF peptides should be useful for applications in which a physician wishes to elevate GH production. Stimulation of G secretion by such hpGRF peptides is of interest in patients with complete or relative GH deficiency caused by underproduction of endogenous GRF. Furthermore, increased GH secretion and its attendant increase in growth should be obtainable in humans or animals with normal GH levels. Furthermore, administration of hpGRF peptides should alter body fat content and modify other GH-dependent metabolic, immunologic and developmental processes. For example, hpGRF peptides may be useful for stimulating anabolic processes in human beings under circumstances such as following the incurring of burns. In another example, hpGRF peptides should be useful in raising commercial animals, such as chickens, pigs, cattle and sheep, to accelerate growth and increase the ratio of protein to fat gained. For administration to humans, synthetic hpGRF peptides should have a purity of at least about 93% and preferably at least 98%. This purity means the intended peptide constitutes the stated weight % of all like peptides and peptide fragments present.

For the administration of synthetic hpGRF peptides to commercial and other animals in order to promote growth and reduce fat content, a purity as low as about 5%, or even as low as 0.1%, may be acceptable.

Synthetic hpGRF peptides or the nontoxic salts thereof, combined with a pharmaceutically acceptable carrier to form a pharmaceutical composition, may be administered to animals, including humans, either intravenously, subcutaneously, intramuscularly, percutaneously, e.g. intranasally, or even orally (at such time that effective couplers or carriers are developed). As used herein, pharmaceutically acceptable should be understood to include veterinarily acceptable. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, pharmaceuticallyacceptable carrier. Usually, the parenteral dosage will be from about 40 nanograms to about 25 micrograms of the peptide per kilogram of the body weight of the host.

It should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminal of the peptide, can be made in accordance with the known experimental practises to date to create fragments that retain all or very substantial portions of the potency of the peptide, and such peptides are considered as being within the scope of the invention. Particular features of the invention are emphasized in the claims which follow.

What is claimed is:

1. A synthetic peptide defined by the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Y wherein Y is $NH_2$, Gln-$NH_2$, Gln-Gln-$NH_2$ or Gln-Gln-Gly-$NH_2$ or a nontoxic salt thereof.

2. A synthetic peptide having the formula of claim 1 wherein Y is $NH_2$.

3. A synthetic peptide having the formula of claim 1 wherein Y is Gln-$NH_2$.

4. A synthetic peptide having the formula of claim 1 wherein Y is Gln-Gln-$NH_2$.

5. A synthetic peptide having the formula of claim 1 wherein Y is Gln-Gln-Gly-$NH_2$.

6. A composition for stimulating the release of GH in an animal comprising an effective amount of a peptide according to claim 1, and an acceptable liquid or solid carrier therefor.

7. A method of stimulating the release of growth hormone in an animal, which comprises administering to said animal an effective amount of a synthetic peptide as defined in claim 1.

8. A method for accelerating the growth of nonhuman animals comprising administering an effective amount of a synthetic peptide as defined in claim 1.

* * * * *

UNITED STATES PATENT AND TRADEMARK OFFICE
CERTIFICATE OF CORRECTION

PATENT NO. : 4,703,035
DATED : October 27, 1987
INVENTOR(S) : Jean E. F. Rivier, et al.

It is certified that error appears in the above-identified patent and that said Letters Patent is hereby corrected as shown below:

Column 2, line 39, Change "WO82" to --WO83--.

Column 3, line 1, "Gln(x$^5$)" should be --Gln(X$^5$)--,

Column 3, line 2, "x$^8$" should be --X$^8$--,

Column 5, line 41, Change "NH $_2$" to --NH$_2$--,

Column 5, line 42, After "stepwise" insert --manner using a Beckman 990 peptide--.

Column 6, line 42, "(x$^5$)" should be --(X$^5$)--.

Column 6, line 43, After "Gln(X$^5$)" insert --Asp(X$^3$)-Ile-Met-Ser(X$^4$)-Arg(X$^6$)-Gln(X$^5$)-Gln(X$^5$)-Gly-X$^8$--, Column 6, line 50, Change "CH$_2$Cl$_2$In" to --CH$_2$Cl$_2$. In--, Column 6, line 66, Change "317" to --3178--.

Column 8, line 34, Change "G" to --GH--.

Signed and Sealed this

Twelfth Day of April, 1988

*Attest:*

DONALD J. QUIGG

*Attesting Officer*       *Commissioner of Patents and Trademarks*

UNITED STATES PATENT AND TRADEMARK OFFICE

CERTIFICATE EXTENDING PATENT TERM
UNDER 35 U.S.C. 156

Patent No.    : 4,703,035

Dated         : October 27, 1987

Inventor(s)   : Jean E.F. Rivier et al

Patent Owner  : The Salk Institute for Biological Studies

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

958 DAYS with all rights pertaining thereto as provided by 35 U.S.C. 156 (b).

I have caused the seal of the Patent and Trademark Office to be affixed this 30th day of December 1991.

Harry F. Manbeck, Jr.
Assistant Secretary and Commissioner
   of Patents and Trademarks